United States Patent
Bollag et al.

(10) Patent No.: US 8,524,692 B2
(45) Date of Patent: Sep. 3, 2013

(54) OCULAR COMPOSITIONS CONTAINING DIOLEOYLPHOSPHATIDYLGLYCEROL AND USES THEREOF

(75) Inventors: Wendy Bollag, Martinez, GA (US); Ding Xie, Augusta, GA (US)

(73) Assignee: Georgia Health Sciences University Research Institute, Inc., Augusta, GA (US)

( * ) Notice: Subject to any disclaimer, the term of this patent is extended or adjusted under 35 U.S.C. 154(b) by 0 days.

(21) Appl. No.: 13/068,007

(22) Filed: Apr. 29, 2011

(65) Prior Publication Data

US 2011/0268787 A1 Nov. 3, 2011

Related U.S. Application Data

(60) Provisional application No. 61/343,449, filed on Apr. 29, 2010.

(51) Int. Cl.
*A61K 31/66* (2006.01)
*A61K 9/127* (2006.01)

(52) U.S. Cl.
USPC .......................... 514/121; 424/450

(58) Field of Classification Search
USPC .......................... 514/121; 424/450
See application file for complete search history.

(56) References Cited

U.S. PATENT DOCUMENTS

| | | | |
|---|---|---|---|
| 2004/0224010 A1* | 11/2004 | Hofland et al. | 424/450 |
| 2007/0026058 A1* | 2/2007 | Pereswetoff-Morath et al. | 424/450 |

OTHER PUBLICATIONS

PubMed Health, Retinal detachment, U.S. National Library of Medicine, Sep. 2011, printed from http://www.ncbi.nlm.nih.gov/pubmedhealth/PMH0002022/?report=printable, 5 pages.*
MedicineNet.com, Your Conrea: Conditions, Symptoms and Treatments, Web MD and Cleveland Clinic, May 26, 2005, printed from http://www.medicinenet.com/script/main/art.asp?articlekey=43321&pf=3&page=2, 5 pages.*
PubMed Health, Astigmatism, U.S. National Library of Medicine, Sep. 3, 2012, printed from http://www.ncbi.nlm.nih.gov/pubmedhealth/PMH0002010/?report=printable, 3 pages.*
Hersh et al. Conductive keratoplasty to treat complications of LASIK and photorefractive keratectomy, Ophthalmology. Nov. 2005;112(11), Epub Sep. 12, 2005, printed from http://www.ncbi.nlm.nih.gov/pubmed/16157379, Abstract only, 2 pages.*
Bodin, et al., "Production of phosphatidylinositol 3,4,5-trisphosphate and phosphatidic acid in platelet rafts: evidence for a critical role of cholesterol-enriched domains in human platelet activation", Biochemistry, 40(50):15290-9 (2001).
Bollag, et al., "A potential role for the phospholipase D2-aquaporin-3 signaling module in early keratinocyte differentiation: production of a phosphatidylglycerol signaling lipid", J Invest Dermatol., 127(12):2823-31 (2007).
Bollag and Zheng, "The Role of Phospholipase D and keratinocyte biology", Trends in Protein Research. New York: Nova Science Publishers, Inc.; 79-118 (2005).

(Continued)

*Primary Examiner* — Gigi Huang
(74) *Attorney, Agent, or Firm* — Pabst Patent Group LLP

(57) ABSTRACT

The present invention provides a method of treating a corneal disorder comprising administering to a patient in need thereof a composition containing pharmaceutically effective amount of dioleoylphosphatidylglycerol and/or palmitoyloleoylphosphatidylglycerol and a pharmaceutically acceptable carrier.

2 Claims, 9 Drawing Sheets

(56) References Cited

OTHER PUBLICATIONS

Brose and Rosenmund, "Move over protein kinase C, you've got company: alternative cellular effectors of diacylglycerol and phorbol esters", J Cell Sci., 115:4399-4411(2002).

Fang, et al., "Phosphatidic acid-mediated mitogenic activation of mTOR signaling", Science, 294:1942-5 (2001).

Gökmen-Polar and Fields, "Mapping of a molecular determinant for protein kinase C betaII isozyme function", J Biol Chem., 273:20261-6 (1998).

Ha and Exton, "Activation of actin polymerization by phosphatidic acid derived from phosphatidylcholine in IIC9 fibroblasts", J Cell Biol., 123:1789-96 (1993).

Hara, et al., "Selectively reduced glycerol in skin of aquaporin-3-deficient mice may account for impaired skin hydration, elasticity, and barrier recovery", J Biol Chem., 277:46616-21 (2002).

Hara and Verkman, "Glycerol replacement corrects defective skin hydration, elasticity, and barrier function in aquaporin-3-deficient mice", PNAS, 100:7360-5 (2003).

Jones, et al., "Phospholipase D and membrane traffic. Potential roles in regulated exocytosis, membrane delivery and vesicle budding", Biochim Biophys Acta, 1439:229-44 (1999).

Kam and Exton, "Phospholipase D activity is required for actin stress fiber formation in fibroblasts", Mol Cell Biol., 21:4055-66 (2001).

Klemm and Elias, "Phosphatidylglycerol-modulated protein kinase activity from human spleen. II. Interaction with phospholipid vesicles", Arch Biochem Biophys., 265:506-13 (1988).

Klemm and Elias, "Purification and assay of a phosphatidylglycerol-stimulated protein kinase from murine leukemic cells and its perturbation in response to IL-3 and PMA treatment", Exp Hematol., 16:855-60 (1988).

Klemm, et al., "Phosphatidylglycerol-modulated protein kinase activity from human spleen. I. Enzyme purification and properties", Arch Biochem Biophys., 265:496-505 (1988).

Kruse, et al., "Phosphatidylglycerol is involved in the dimerization of photosystem II", J Biol Chem., 275:6509-14 (2000).

McPhail, et al., "A novel protein kinase target for the lipid second messenger phosphatidic acid", Biochim Biophys Acta., 1439:277-90 (1999).

Murray and Fields, "Phosphatidylglycerol is a physiologic activator of nuclear protein kinase C.", J Biol Chem., 273:11514-20 (1998).

Piccotti, et al., "Exogenous phospholipids specifically affect transmembrane potential of brain mitochondria and cytochrome C release", J Biol Chem 277:12075-81(2002).

Pietromonaco, et al., "Protein kinase C-theta phosphorylation of moesin in the actin-binding sequence", J Biol Chem 273:7594-7603 (1998).

Rizzo, "The recruitment of Raf-1 to membranes is mediated by direct interaction with phosphatidic acid and is independent of association with Ras", J Biol Chem 275-23911-8(2000).

Rizzo, "Phospholipase D and its product, phosphatidic acid, mediate agonist-dependent raf-1 translocation to the plasma membrane and the acitivation of the mitogen-activated protein kinase pathway", J Biol Chem 274:1131-9 (1999).

Sato, et al., "Requirement of phosphatidylglycerol for photosynthetic function in thylakoid membranes", PNAS, 97:10655-60 (2000).

Sergeant, et al., "Phosphatidic acid regulates tyrosine phosphorylating activity in human neutrophils: enhancement of Fgr actifity", J Biol Chem., 276:4737-46 (2001).

Yokozeki, et al., "Phosphatidic acid-dependent phosphorylation of a 29-kDa protein by protein kinase Calpha in bovine brain cytosol", J Neurochem 71:410-17 (1998).

Yuspa, et al., "Expression of murine epidermal differentiation markers is tightly regulated by restricted extracellular calcium concentrations in vitro", J Cell Biol 109:1207-17 (1989).

Zheng, et al., "Aquaporin 3 colocates with phospholipase d2 in caveolin-rich membrane microdomains and is downregulated upon keratinocyte differentiation", J Invst Dermatol 121:1487-95 (2003).

\* cited by examiner

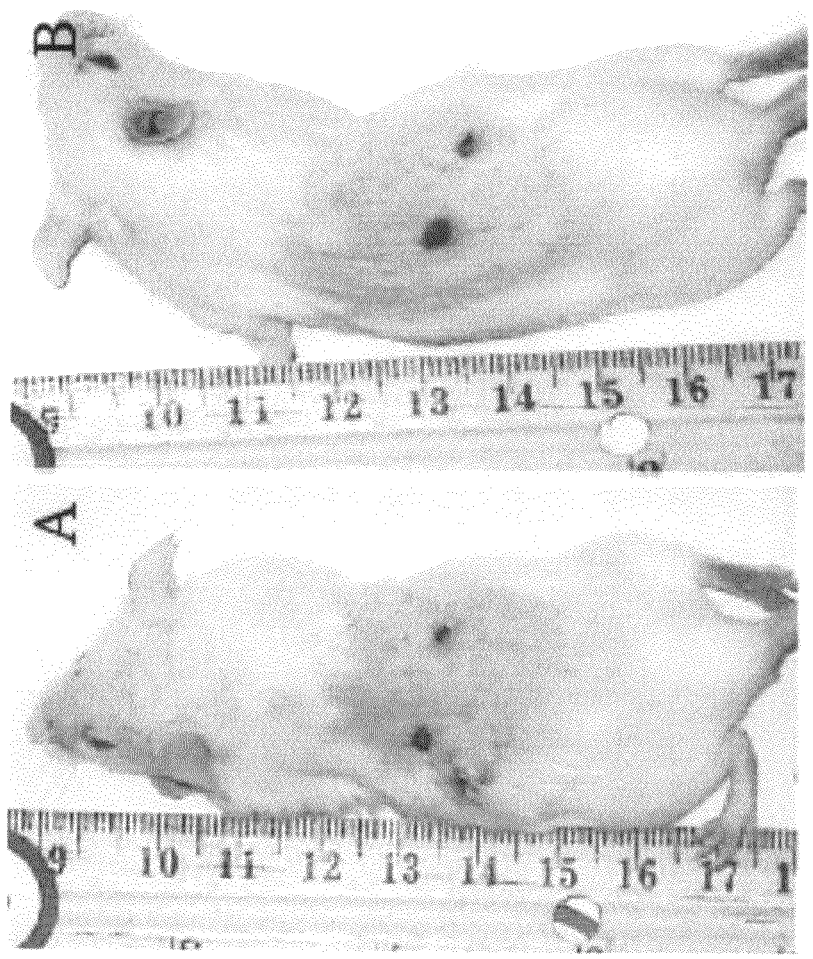

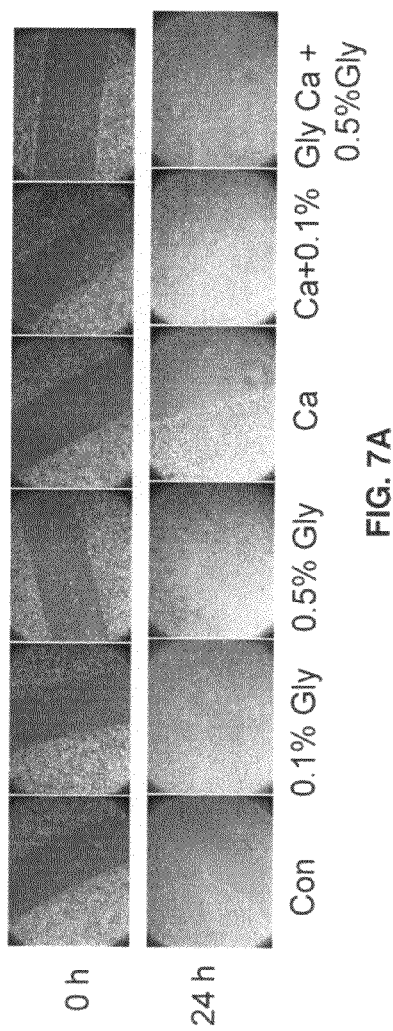
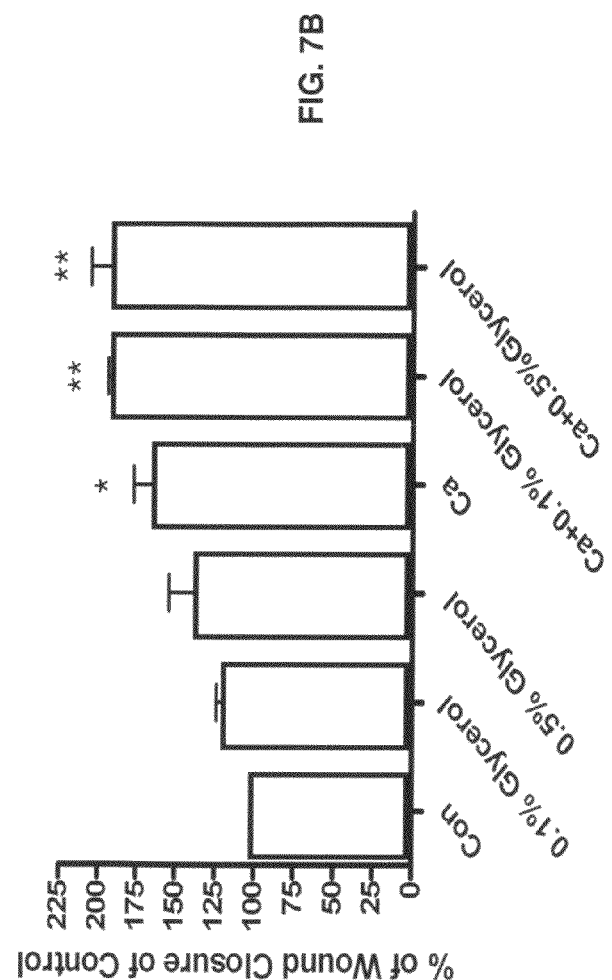

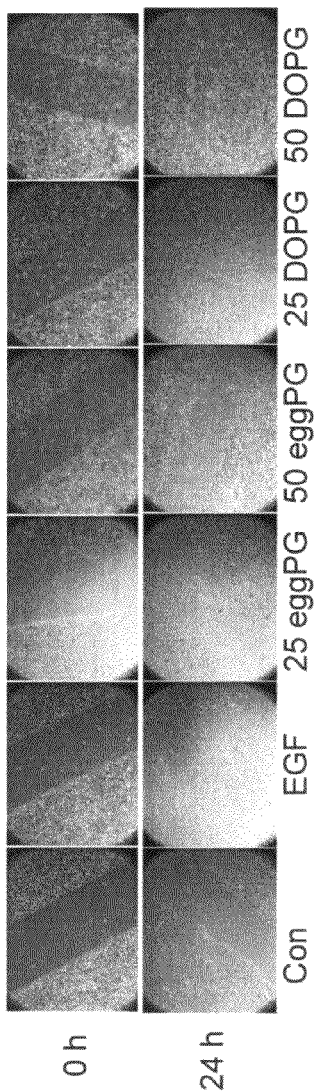
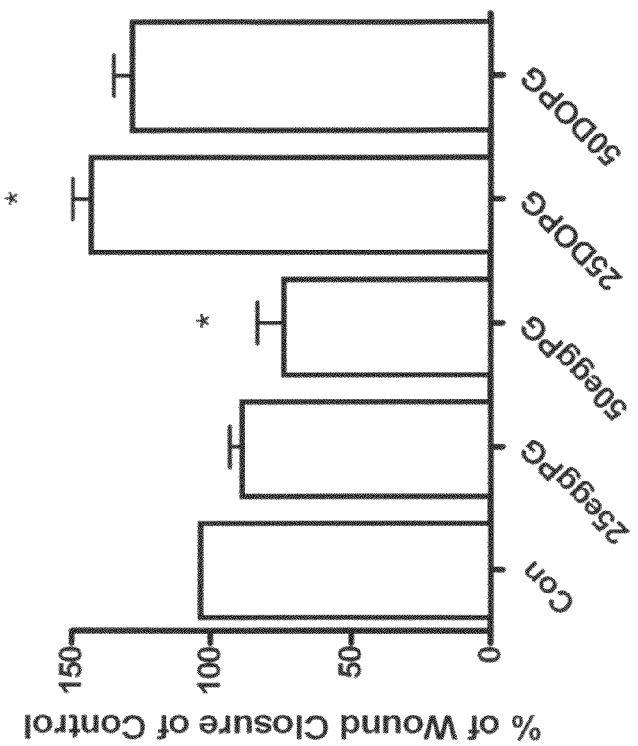

OCULAR COMPOSITIONS CONTAINING DIOLEOYLPHOSPHATIDYLGLYCEROL AND USES THEREOF

CROSS-REFERENCE TO RELATED APPLICATIONS

This nonprovisional applications claims benefit of priority under 35 U.S.C. §119(e) of provisional application U.S. Ser. No. 61/343,449, filed Apr. 29, 2010, now abandoned, the entirety of which is hereby incorporated by reference

FEDERAL FUNDING LEGEND

This invention was made with government support under Grant Numbers AR45212 and AR55022 awarded by the National Institutes of Health. The government has certain rights in the invention.

BACKGROUND OF THE INVENTION

1. Field of the Invention

The present invention relates to the fields of ocular biology and treatments. More specifically, the present invention relates to, inter alia, methods for treating corneal disorders.

2. Description of the Related Art

Blindness from corneal etiologies is a serious global issue limiting the productivity and quality of life of approximately 4.9 million people around the world (1). The cornea is an avascular, translucent tissue that serves to allow the entry of light into the visual system and to focus the incoming rays of the visible spectrum. The outermost layer of the cornea, the stratified squamous epithelium, is integral in maintaining optical clarity and defending against microbial infection. The air-tear interface is the most important refracting surface in the ocular visual apparatus, and an irregular corneal epithelial surface results in substantial degradation of optical clarity, as is seen clinically with corneal abrasions, diabetic epitheliopathy, recurrent corneal erosions, dry eye syndrome, neurotrophic keratopathy, Stevens Johnson syndrome, ocular cicatricial pemphigoid, exposure keratopathy, and corneal transplantation, among others. Each of these corneal disease processes significantly compromises vision and consumes considerable resources in the United States in terms of work productivity, medical and pharmaceutical costs and quality of life.

The barrier function of the corneal epithelium serves a crucial role in maintaining ocular health by preventing microbial infection. Following trauma and chemical injuries of the corneal epithelium, the eye is markedly susceptible to infectious keratitis. Following surgical violation of the corneal epithelium, as occurs in cataract surgery, corneal transplantation surgery and refractive surgery [i.e., laser in situ keratomileusis (LASIK) and photorefractive keratectomy (PRK)], the risk of keratitis increases significantly. For example, keratitis after LASIK surgery was recently reported to occur in 2.66% of operated eyes (2). A tool to stimulate corneal epithelial healing would have a significant impact on visual morbidity from common ocular ailments, would improve visual rehabilitation after trauma and chemical injuries and would make surgical manipulations of the cornea safer and more reliable.

Keratinocytes form the epithelium of the skin, the epidermis. These cells undergo a distinct pattern of differentiation that is essential for the function of the skin as a protective barrier. This pattern is characterized by growth arrest and expression of the mature keratins 1 and 10 in the first differentiated layer of the epidermis, the spinous layer. Early differentiation in the spinous layer is followed by late differentiation in the granular layer accompanied by expression of proteins that are essential for the formation of the cornified envelope and corneocytes. The corneocytes constitute the outer layer of the epidermis, the stratum corneum, and give skin its resistance to mechanical stress (3). This program of keratinocyte differentiation can be regulated in vitro by the extracellular calcium concentration, with low calcium concentrations (<90 µM) promoting a proliferative phenotype and elevated calcium concentrations (>100 µM) stimulating differentiation (4, 5). The effects of extracellular calcium levels are thought to be physiologically relevant, since a calcium gradient (low in the basal layer and progressively higher in suprabasal layers) has also been observed in the epidermis in situ (6-9). Although the mechanism responsible for generation of this calcium gradient is unknown, presumably the extracellular calcium concentration regulates keratinocyte differentiation via activation of the G protein-coupled calcium-sensing receptor (CaSR) expressed in these cells (10-12).

Corneal epithelial cells exhibit many similarities to epidermal keratinocytes. Both cells form stratified epithelia exposed to the environment and express many of the same genes/proteins [e.g., the immature keratin 14 (13), the differentiation markers, involucrin, loricrin and transglutaminase (14, 15) and aquaporin-3 (16, 17)]. Elevated extracellular calcium concentrations inhibit the proliferation of both cell types (18), which can be grown in vitro in the same culture medium (15). Both cell types exhibit a programmed pattern of differentiation, including expression of mature keratins (keratins 1 and 10 in the epidermis and keratins 3 and 12 in the cornea) (18, 19). In addition, both cell types exhibit a migratory phenotype that is induced by epithelial wounding (20). Thus, it seems likely that the function of these cells is regulated by similar mechanisms.

Phospholipase D (PLD) hydrolyzes phospholipids, primarily phosphatidylcholine, to generate phosphatidic acid, which can be dephosphorylated by lipid phosphate phosphatases to yield diacylglycerol. Indeed, in several cell systems, phospholipase D activity has been shown to underlie at least a portion of agonist-induced sustained diacylglycerol production (21, 22). Diacylglycerol, in turn, is known to function as a second messenger (23), as is phosphatidic acid itself (24-30) and (31, 32). However, of interest is the fact that phospholipase D can also, in the presence of primary alcohols, catalyze a transphosphatidylation reaction to generate a phosphatidylalcohol. In fact, phospholipase D utilizes alcohols such as ethanol and butanol to yield phosphatidylethanol or -butanol (33), even when these alcohols are at low concentration.

In keratinocytes, one isoform of phospholipase D, phospholipase D2 (PLD2) is co-localized with the glycerol channel aquaporin-3 (AQP3) (34), and this isoform may be responsible for the observation that glycerol can be utilized by a phospholipase D enzymatic activity to generate in keratinocytes a potentially novel signaling lipid, phosphatidylglycerol (PG) (35, 36). Thus, AQP3 may provide glycerol to phospholipase D2 for the production of phosphatidylglycerol via the transphosphatidylation reaction, and this phosphatidylglycerol acts as a novel lipid signaling molecule to regulate early keratinocyte differentiation (36), as well as corneal epithelial cell function. Manipulations that alter the function of this PLD2/AQP3/PG signaling module can inhibit epidermal keratinocyte proliferation. Thus, stimulating phosphatidylglycerol formation by increasing AQP3 expression decreases the promoter activity of a marker of the proliferative basal layer (keratin 5) and enhances the promoter activity of a marker of differentiation (keratin 10) (35). Similarly, increasing phosphatidylglycerol production by raising the extracellular glycerol concentration also reduces keratinocyte proliferation, and direct provision of phosphatidylglycerol in the form of liposomes also inhibits the growth of rapidly proliferating keratinocytes (35). Interestingly, application of phosphatidylglycerol liposomes to slowly growing cells increases proliferation (35), suggesting that phosphatidylglycerol liposomes normalize keratinocyte function, accelerating growth in slowly proliferating cells and decreasing proliferation in rapidly growing cells. The data suggest that this signaling module also functions in corneal epithelial cells to produce phosphatidylglycerol (PG) and alter cell function.

How might phosphatidylglycerol act to alter keratinocyte and/or corneal epithelial cell function? One enzyme regulated by phosphatidylglycerol is PKC-_II; thus, in human leukemia cells PKC-βII is activated by nuclear phosphatidylglycerol, and this activation is required for cell cycle progression (47, 48). PKC-θ is also reportedly phosphatidylglycerol-activated (49) and mediates phosphorylation of the actin-binding domain of moesin. Another possible phosphatidylglycerol responsive protein kinase is "PK-P", which has been isolated from human spleen (50-52). Alternatively, it is possible that phosphatidylglycerol can be reincorporated into the local membrane microdomains (lipid rafts) to regulate the organization of signaling molecules, such as the EGF receptor. Consistent with this idea, phosphatidic acid and phosphoinositide 3-kinase products have been reported to be concentrated in lipid rafts when platelets are stimulated by thrombin (53). Phosphatidylglycerol may also function by facilitating the interaction and function of membrane proteins, as has been observed in thylakoid membranes of spinach and a cyanobacterium, for which photosystem assembly requires phosphatidylglycerol (54, 55). Finally, phosphatidylglycerol and diphosphatidylglycerol (more commonly known as cardiolipin) are known to be important lipids in mitochondria. For instance, phosphatidylglycerol and cardiolipin restore the mitochondrial membrane potential in depleted mitochondria (56).

Thus, there is a continued need in the art for identification of compositions and methods to treat corneal disorders. The present invention fulfills this long-standing need and desire in the art.

SUMMARY OF THE INVENTION

The present invention is directed to a method of treating a corneal disorder comprising administering to a patient in need thereof a composition containing a pharmaceutically effective amount of dioleoylphosphatidylglycerol and/or palmitoyloleoylphosphatidylglycerol and a pharmaceutically acceptable carrier.

In another embodiment, the present invention provides a method of treating an eye wound in a subject, comprising the steps administering to the eyes of said subject an effective amount of dioleoylphosphatidylglycerol and/or palmitoyloleoylphosphatidylglycerol and a pharmaceutically acceptable carrier.

In yet another embodiment, the present invention provides an ocular composition consisting essentially of dioleoylphosphatidylglycerol.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

The egg phosphatidylglycerol used (47) is actually a mixture of different phosphatidylglycerol species composed of various fatty acids, with palmitate (with 16 carbons and no double bonds, i.e. 16:0) and oleate (18:1) most abundant. Based on the idea that phosphatidylglycerol liposomes can normalize keratinocyte function, it was determined the phosphatidylglycerol species that were most effective at inhibiting the growth of rapidly proliferating keratinocytes and stimulating the proliferation of slowly dividing cells. Different PG species were effective in growth inhibition versus promotion. Phosphatidylglycerol species containing polyunsaturated fatty acids were most effective at inhibiting rapidly proliferating keratinocytes, whereas the growth promoting effect in slowly dividing keratinocytes was most effectively induced by PG species with monounsaturated fatty acids (with or without saturated fatty acids). Palmitoyl, arachidonyl-PG (16:0, 20:4), palmitoyl, linoleoyl-PG (16:0, 18:2), dilinoleoyl-PG (18:2, 18:2) and soy phosphatidylglycerol (a phosphatidylglycerol mixture with a large proportion of polyunsaturated fatty acids) were particularly effective at inhibiting proliferation in rapidly dividing keratinocytes. Palmitoyl, oleoyl-PG (16:0, 18:1) and dioleoyl-PG (18:1, 18:1) were especially effective proliferative phosphatidylglycerol species. This result indicates that different phosphatidylglycerol species may signal to different effector enzymes to differentially alter keratinocyte growth, with some PG-binding proteins promoting differentiation and others stimulating proliferation.

FIGS. 2A-2B show wound healing of full-thickness punch biopsies of mouse skin. Two full-thickness skin punch biopsies of ~4 mm were made on the backs of ICR CD-1 mice. For each mouse one wound was either (FIG. 2A) untreated (left) or treated with 2M glycerol in water (right) or (FIG. 2B) treated with phosphate-buffered saline lacking divalent cations (PBS, left) or PBS containing 100 μg/mL phosphatidylglycerol, prepared as liposomes via bath sonication (right). The rate of wound healing was then followed over 4 days by digital photography and computer image analysis. Shown is the extent of wound healing on day 4 for two representative mice. Both male and female mice were used and the results pooled.

Figure 1A:
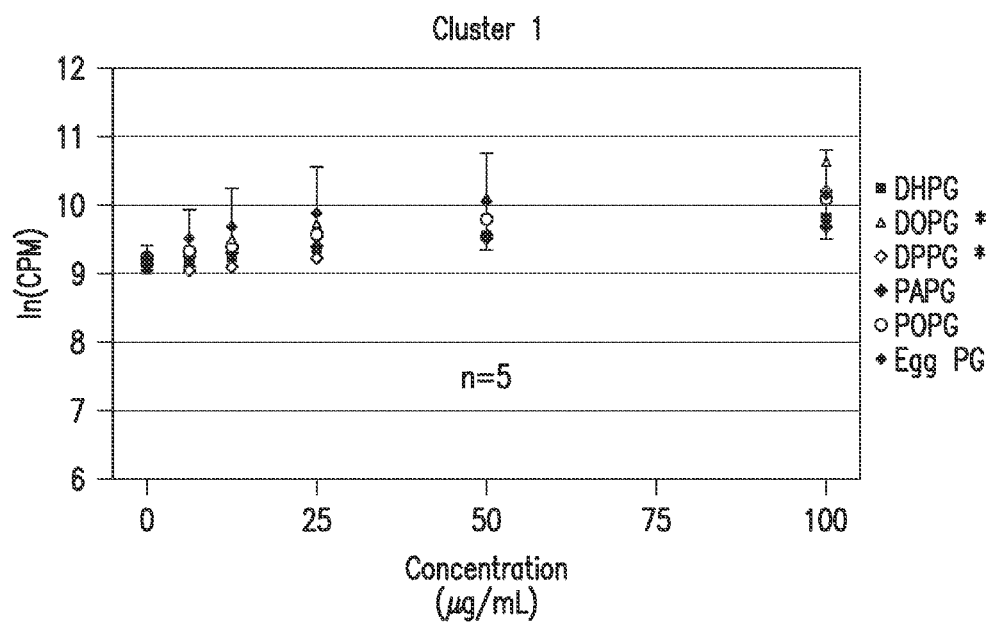
FIGS. 1A-1D show that different phosphatidylglycerol species effectively inhibit or promote proliferation in rapidly or slowly dividing keratinocytes, respectively. Keratinocytes were treated for 24 hours with the indicated concentrations of different phosphatidylglycerol species, prepared via bath sonication of phospholipid in serum-free keratinocyte medium. [$^3$H]Thymidine incorporation into DNA was then determined in duplicate and averaged. All data were transformed prior to analyses to improve assumptions of normality and additivity for the models to be used. Experiments were grouped that had different responses to egg phosphatidylglycerol using finite mixture regression models and the flexmix package in R (1). This method clusters each experiment by the regression fit between ln(CPM) and ln(concentration), grouping cultures with similar regression lines in the same cluster. The number of clusters was determined using the Bayesian information criterion (BIC). A mixed model analysis of variance was used, conducted using the Proc Mixed procedure in SAS 9.13, separately for each of the grouped clusters to determine how the different phosphatidylglycerol species affected the relationship between cell proliferation and phosphatidylglycerol concentration. The model used for this analysis of variance included phosphatidylglycerol species as a fixed effect that potentially interacted with ln(concentration), and random coefficients for each culture/experiment. The number of experiments segregating into each cluster are indicated and *$p<0.05$ versus the response to egg phosphatidylglycerol liposomes.
Figure 1B:
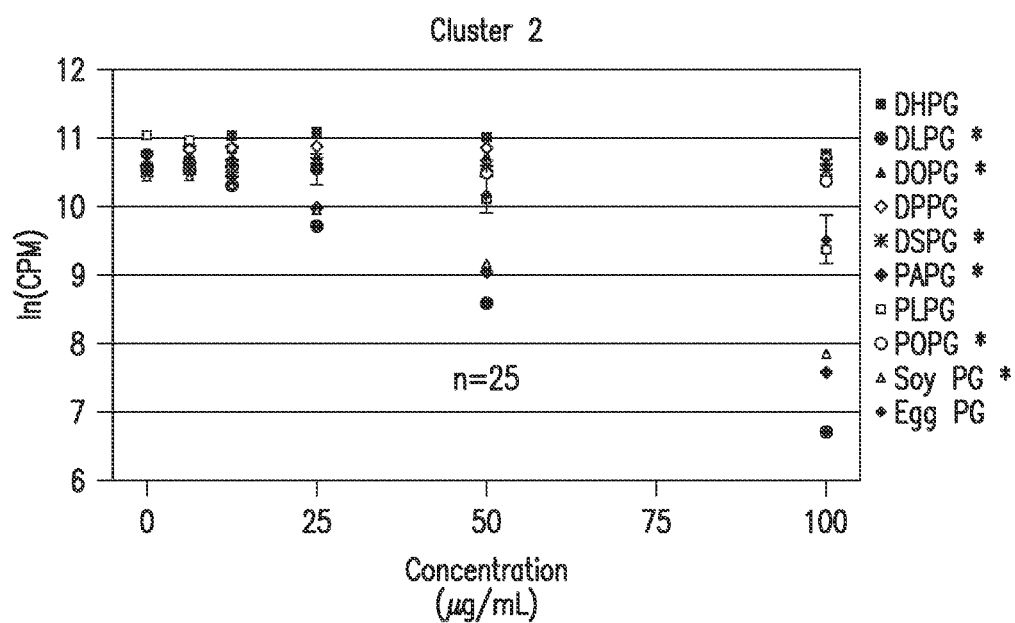
Figure 1C:
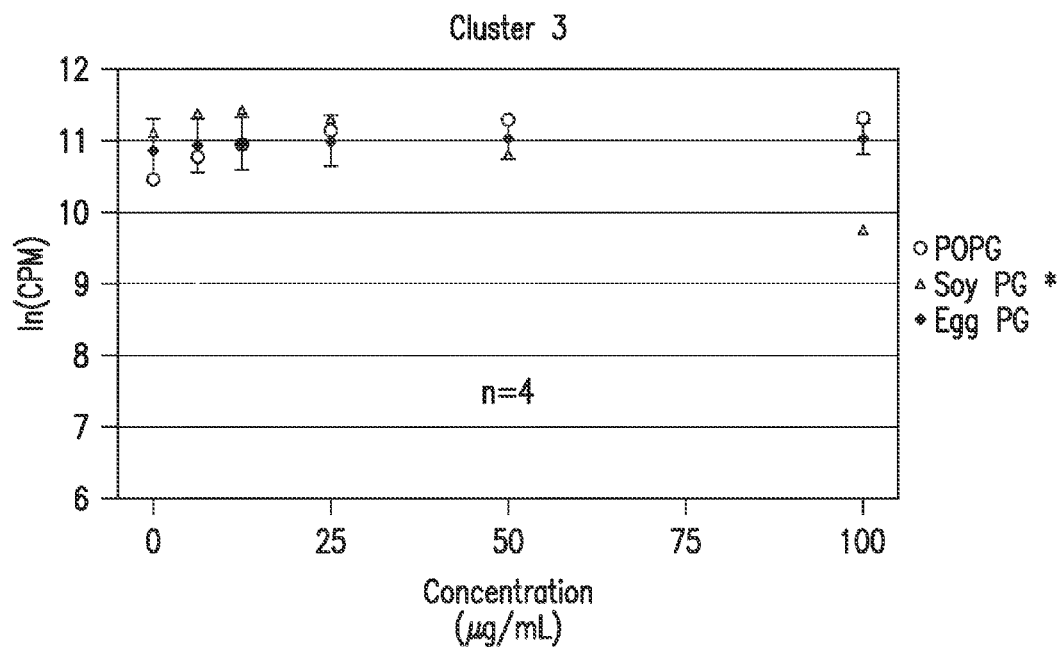
Figure 1D:
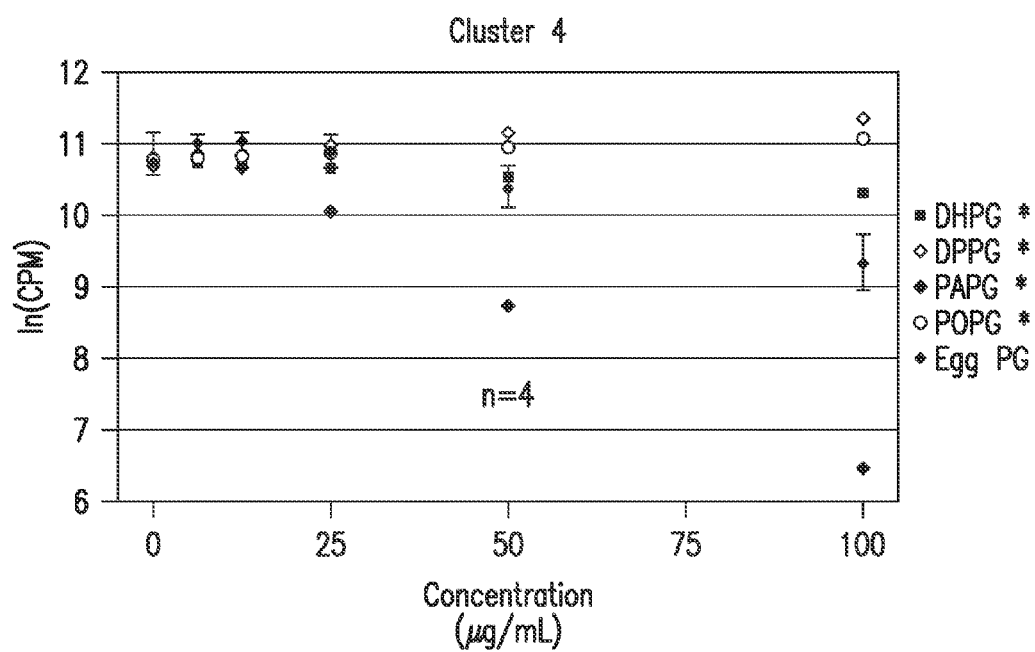
Figure 3:
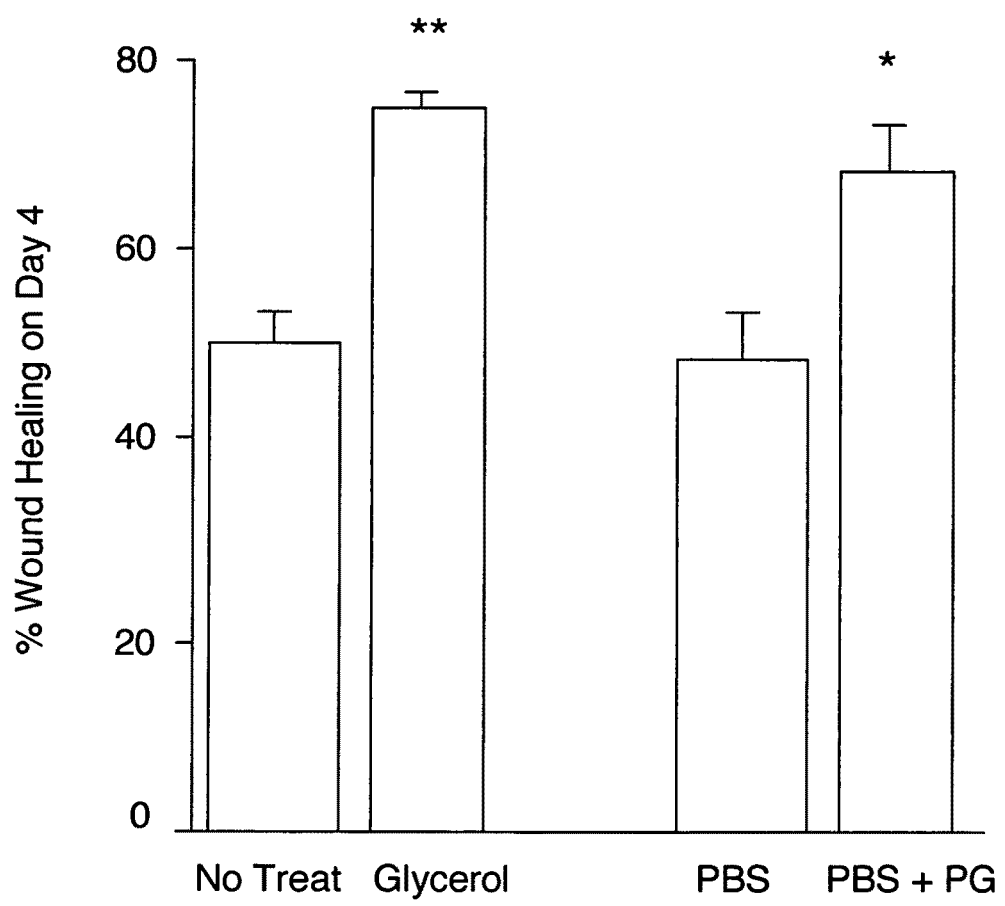

FIG. 3 shows that glycerol and phosphatidylglycerol liposomes accelerate wound healing of full-thickness punch biopsies of mouse skin in vivo. Two full-thickness skin punch biopsies of ~4 mm were made on the backs of a total of sixteen ICR CD-1 mice (two groups of four male and four female mice). For each mouse one wound was either (1) untreated (No Treat) or treated with 2M glycerol in water (Glycerol) or (2) treated with PBS (PBS) or PBS containing 100 μg/mL PG, prepared as liposomes via bath sonication (PBS+PG). The rate of wound healing was then followed over 4 days by digital photography and computer image analysis, and percentage of wound healing on day 4 relative to day 1 for each of the four groups is shown. The experiment was repeated on a second group of mice, with the opposite side exposed to glycerol or PG liposomes. No difference was observed between male and female mice so the results were pooled. Results represent the means±SEM of 8 mice for each condition; *$p<0.02$ versus treatment with PBS; **$p<0.001$ versus no treatment.

Figure 4B:
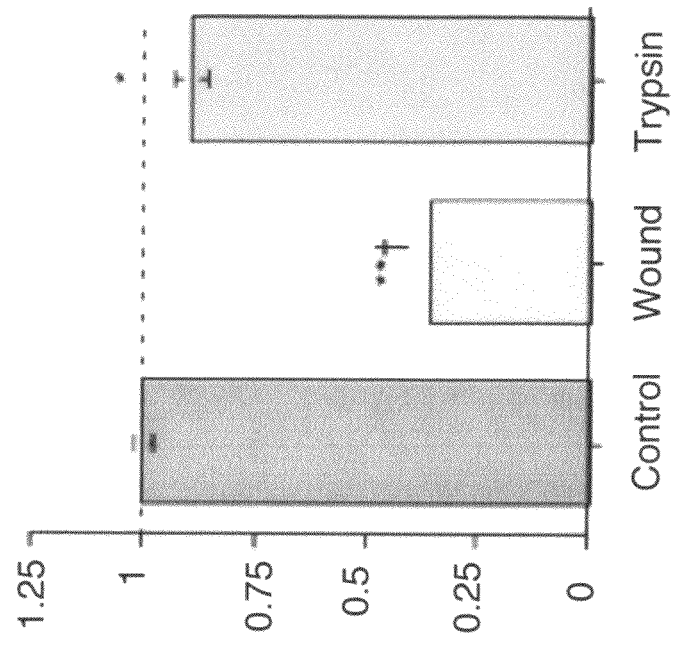
Figure 4A:
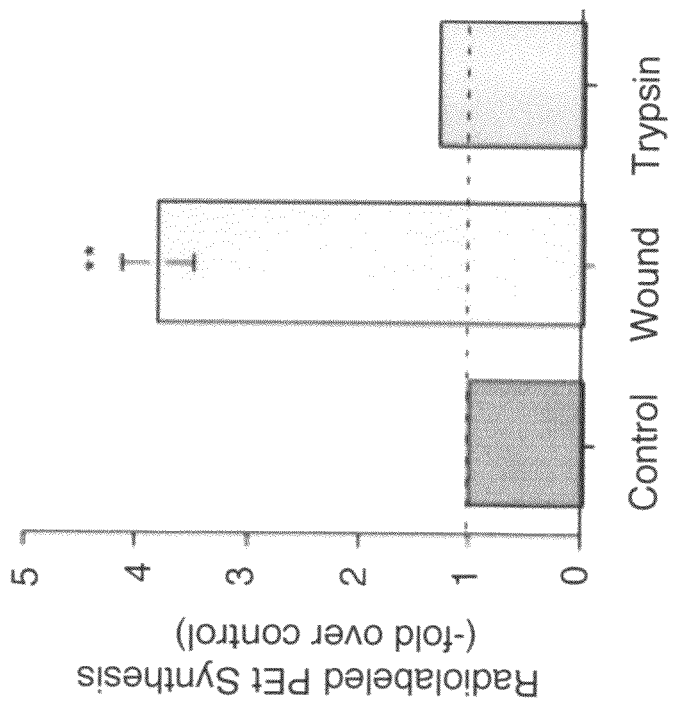

FIGS. 4A-4B shows that cell wounding, but not trypsinization, activates phospholipase D (PLD) but decreases phosphatidylglycerol synthesis. FIG. 4A: [$^3$H]Oleate-prelabeled keratinocytes were treated with 1% ethanol immediately prior to removal of the cells from the substratum with a cell lifter or trypsinization (with 0.25% trypsin) and incubation for 15 minutes. Reactions were terminated by the addition of 0.2% SDS containing 5 mM EDTA, and [$^3$H]phosphatidylethanol was extracted, separated by thin-layer chromatography and quantified. Values are expressed as -fold over the control and represent the means (±SEM) of 8 samples from 4 separate experiments; **$p<0.01$ versus the control value. FIG. 4B: Cells were treated with [$^{14}$C]glycerol immediately prior to cell lifting and incubation for 15 minutes. Reactions were terminated by the addition of 0.2% SDS containing 5 mM EDTA, and [$^{14}$C]PG was extracted, separated by thin-layer chromatography and quantified. Values are expressed as -fold over the control and represent the means (±SEM) of 3 separate experiments performed in duplicate; *$p<0.01$. **$p<0.001$ versus the control value; †$p<0.001$ versus trysinization. In both cases, similar results were obtained when cells were more gently lifted from the dish using a rubber policeman.

Figure 5:
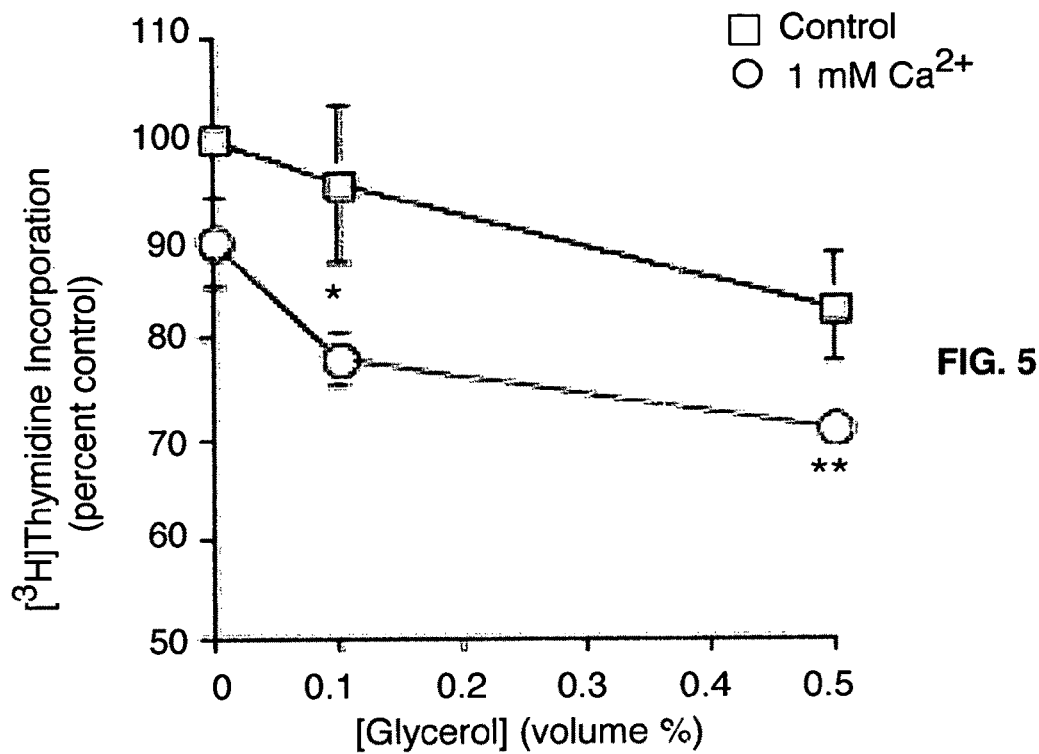

FIG. 5 shows that glycerol and an elevated extracellular calcium concentration act together to inhibit DNA synthesis in proliferating human corneal epithelial cells. SV40-immortalized human corneal epithelial cells at approximately 50-60% confluence were treated for 24 hours with dKSF medium containing no calcium supplementation (Control; 90 μM calcium) or supplemented with 1 mM calcium (1 mM $Ca^{2+}$) in the presence and absence of the indicated concentrations of glycerol. [$^3$H]Thymidine incorporation into DNA was then determined. Values represent the means±SEM of 3 separate experiments performed in duplicate; *$p<0.05$, **$p<0.01$ versus the control value.

Figure 6:
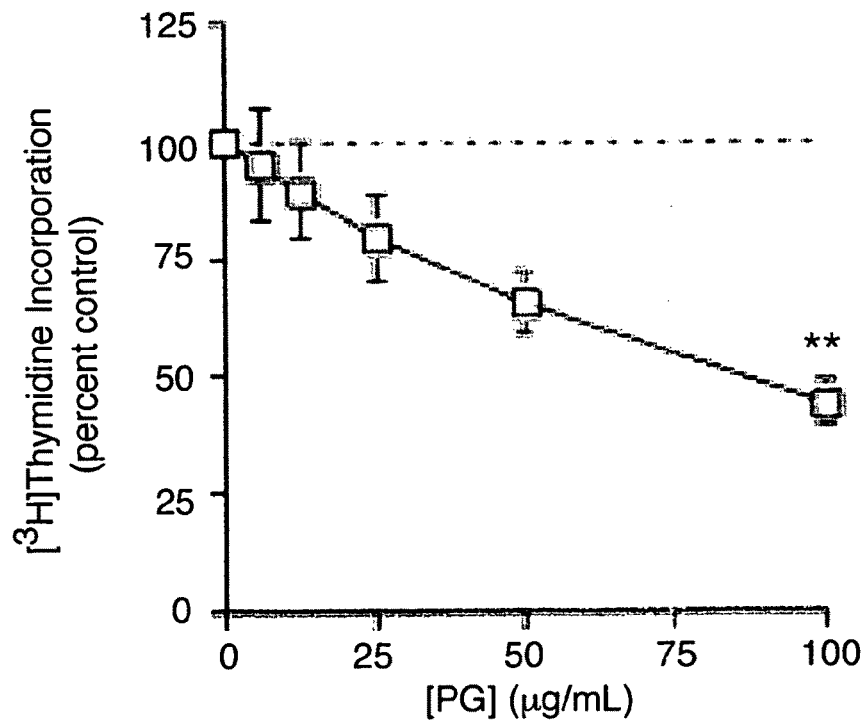

FIG. 6 shows that liposomes composed of egg phosphatidylglycerol (a mixture of phosphatidylglycerol species with different fatty acid compositions) inhibit DNA synthesis in proliferating human corneal epithelial cells. SV40-immortalized human corneal epithelial cells were cultured in a 1:1 mixture of defined keratinocyte serum free (dKSF) medium (Gibco) and minimum essential medium (Cellgro) until approximately 70% confluent. These near-confluent cells were then treated for 24 hours with dKSF medium containing the indicated concentrations of phosphatidylglycerol liposomes, prepared via bath sonication of PG in dKSF. [$^3$H] Thymidine incorporation into DNA was then determined. Values represent the means±SEM of 4 separate experiments performed in duplicate; *$p<0.01$ versus the control value.

FIGS. 7A-7B show the effect of glycerol on wound closure in transformed human corneal epithelial cells. SV40-immortalized human corneal epithelial cells were cultured in a 1:1 mixture of defined keratinocyte serum free (dKSF) medium (Gibco) and minimum essential medium (Cellgro) until confluent. A pipet tip was then used to create a scratch wound in the confluent monolayer. Cells were rinsed with PBS to remove unattached and damaged cells and photographed under the microscope. The medium was replaced with dKSF containing the indicated additions (Ca corresponds to 1 mM $Ca^{2+}$). Cells were incubated for 24 hours and photographed again. Percent wound closure was calculated as the change in width of the scratch wound compared to the size of the initial wound and was expressed relative to the control (medium with no additions containing 90 μM $Ca^{2+}$); *$p<0.05$; **$p<0.01$ versus the control (n=3).

FIGS. 8A-8B show the effect of egg phosphatidylglycerol and dioleoylphosphatidylglycerol on wound closure in transformed human corneal epithelial cells. SV40-immortalized human corneal epithelial cells were cultured in a 1:1 mixture of defined keratinocyte serum free (dKSF) medium (Gibco) and minimum essential medium (Cellgro) until confluent. A pipet tip was then used to create a scratch wound in the confluent monolayer. Cells were rinsed with PBS to remove unattached and damaged cells and photographed under the microscope. The medium was replaced with dKSF containing the indicated concentrations of liposomes composed of egg phosphatidylglycerol or dioleoylphosphatidylglycerol, prepared via bath sonication of PG in dKSF. Cells were incubated for 24 hours and photographed again. Percent wound closure was calculated as the change in width of the scratch wound compared to the size of the initial wound and was expressed relative to the control (medium with no additions); *$p<0.05$ versus the control (n=3).

Figure 9:
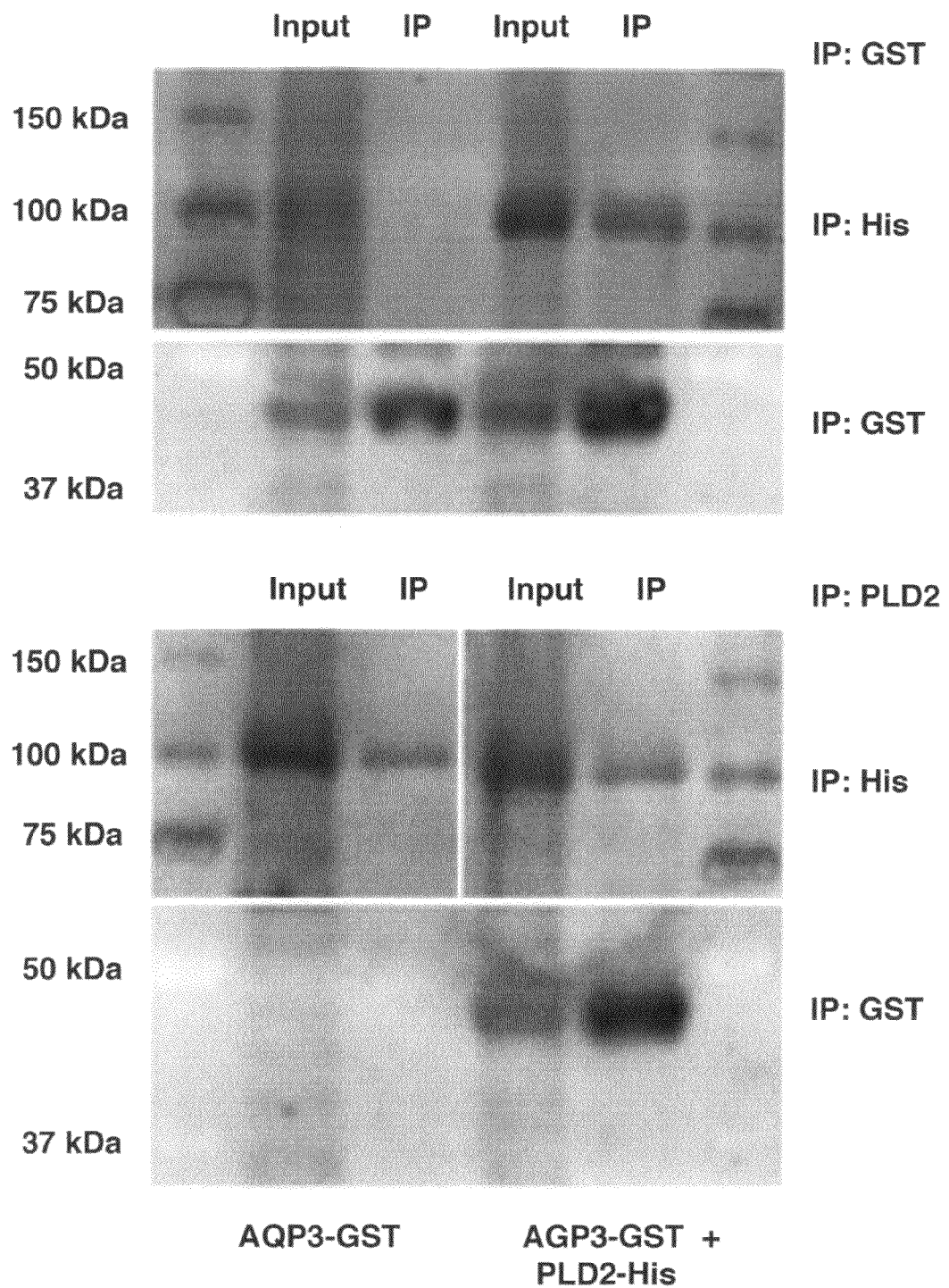

FIG. 9 shows baculovirus-expressed AQP3 and PLD2 coimmunoprecipitate from Sf9 insect cells. Sf9 insect cells were infected with baculovirus expressing GST-tagged AQP3 (AQP3-GST) alone or both AQP3-GST and His-tagged PLD2 (PLD2-His) as indicated. Sf9 lysates were then immunoprecipitated (IP) with anti-GST antibody or anti-PLD2 antibody and the immunoprecipitates analyzed by immunoblotting (IB) using antibodies recognizing GST or His as indicated. A 1/10 volume of lysate was similarly analyzed.

DETAILED DESCRIPTION OF THE INVENTION

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any device or method described herein can be implemented with respect to any other device or method described herein. As used herein, the term "or" in the claims refers to "and/or" unless explicitly indicated to refer to alternatives only or the alternatives are mutually exclusive, although the disclosure supports a definition that refers to only alternatives and "and/or". As used herein, the term "contacting" refers to any suitable method of bringing a compound or a composition into contact with a cell. In vitro or ex vivo this is achieved by exposing the cell to the compound or agent in a suitable medium. For in vivo applications, any known method of administration is suitable as described herein. As used herein, the term "subject" refers to any human or non-human recipient of the composition described herein.

The present invention is directed to a method of treating a corneal disorder comprising administering to a patient in need thereof a composition containing a pharmaceutically effective amount of dioleoylphosphatidylglycerol and a pharmaceutically acceptable carrier. Representative examples of corneal disorders include but are not limited to a corneal ulcer, a corneal erosion, keratitis or dry eye. In one form, the composition may be administered in a dosage form of an eye drop. Preferably, the dioleoylphosphatidylglycerol is contained in said composition in a concentration of from about 10 µg/mL to about 1000 µg/mL (or 0.001% to 0.1%). Representative pharmaceutically acceptable carriers include a surface active agent, a protein, and/or a carrier liquid. In one embodiment, the composition further comprises one or both of an antibiotic agent and an anti-inflammatory agent. In another embodiment, the corneal disorder is subsequent to mechanical injury resulting from laser in situ keratomeliusis or photorefractive keratectomy. The composition may take any form as is well known to one having ordinary skill in this art including but not limited to a capsule, a bead, a liposome, a sphere, a dissolvable biocompatible polymer sheet, and combinations thereof.

The present invention is further directed to a method of treating an eye wound in a subject, comprising the step of administering to the eyes of said subject an effective amount of dioleoylphosphatidylglycerol and a pharmaceutically acceptable carrier. Any pharmaceutically acceptable carrier known to one having ordinary skill in this art may be used, including water. In one form, this method reduces contact lens intolerance. Adjusting the dose of dioleoylphosphatidylglycerol is well within the ability of one having ordinary skill in this art and will likely depend on the actual disorder or injury being treated but an effective amount will typically fall within the range of 10 µg/mL to 1000 µg/mL (or 0.001% to 0.1%). In one embodiment of this method of the present invention, the administration is topical administration to the ocular surface of the eyes. Representative examples of types of topical administration include administration via a carrier vehicle selected from the group consisting of drops of liquid, liquid wash, gels, ointments, sprays and liposomes. Alternatively, the topical administration is infusion of said dioleoylphosphatidylglycerol to said ocular surface via a device selected from the group consisting of a pump-catheter system, a continuous or selective release device, and a contact lens.

The present invention is further directed to an ocular composition consisting essentially of dioleoylphosphatidylglycerol. A representative composition is a liposomal composition, types of which are very well known in the art.

The following example(s) are given for the purpose of illustrating various embodiments of the invention and are not meant to limit the present invention in any fashion.

Example 1

Methods

Specific methods used include measurement of PLD activity and phosphatidylglycerol synthesis (46, 62, 66); co-immunoprecipitation and Western blot analysis of AQP3 and PLD2 (34); sucrose density ultracentrifugation of membrane fractions (34), PCR and RT-PCR amplification and cloning.

Cell Culture: SV40-immortalized human corneal epithelial cells were obtained from Dr. Fu-Shin Yu (Wayne State University, Detroit, Mich.). The cells are cultured in defined keratinocyte serum-free (dKSF) medium (Gibco) and passaged following trypsinization from the culture dish. Experiments are performed in dKSF medium (90 µM calcium) supplemented with the agents of interest (phosphatidylglycerol liposomes, glycerol, elevated extracellular calcium concentration, etc.).

[$^3$H]Thymidine Incorporation Assays: [$^3$H]Thymidine incorporation into DNA is measured as described (62).

Western Blot Analysis: AQP3, PLD2, keratin 3 and involucrin protein expression are monitored by western blot analysis as in (34, 94). Actin levels are measured as a protein loading control.

Membrane Microdomain Isolation. Membrane microdomains are isolated by fractionation on sucrose gradients following cell lysis by sodium carbonate, as in (34), and the fractions analyzed by immunoblotting.

Cloning and Sequencing: Recombinant DNA techniques are essentially as in (95). Sequences are verified via automated sequencing by the Medical College of Georgia Molecular Biology Core Facility.

PLD Activity Assay: PLD activity is measured by examining the production of [$^3$H]phosphatidic acid and phosphatidylethanol, in the presence of 0.5% ethanol in [$^3$H]oleate-labeled cells, as described in (66, 96), or in non-labeled cells upon addition of [$^3$H] or [$^{14}$C]glycerol as in (35, 46).

Corneal Wound Healing Assay: Rabbits (4-5 kg) are anesthetized with ketamine/xylazine and corneal wounds made by centrally applying 6 mm filters soaked in n-haptanol for 1 minute, followed by thorough irrigation of the eye with saline to remove the corneal epithelium. Agents of interest in sterile saline is applied to the eye three times per day and wound healing followed by staining with fluorescein (1% sodium fluorescein), digital photography under filtered green light and computerized image analysis twice a day, as in (79).

Statistical Analysis: Experiments are repeated a minimum of three times, when possible in duplicate or triplicate. Statistical analysis will be performed using the statistics program InStat (GraphPad). ANOVA with a Student-Neumann-Keuls post-hoc test is performed.

PG Regulates Corneal Epithelial Cell Function and is Generated by the PLD2/AQP3 Signaling Module The ability of glycerol and phosphatidylglycerol liposomes to decrease corneal epithelial cell proliferation, (b) whether PLD2 and AQP3 colocalize in caveolin-rich membrane microdomains in corneal epithelial cells and (c) the ability of regulators of corneal epithelial cell function (e.g., extracellular calcium concentration) to stimulate phosphatidylglycerol production is determined.

PG Liposomes Promote Wound Healing In Vitro and In Vivo

Phosphatidylglycerol can accelerate epidermal wound healing in a mouse model in vivo. In AQP3 knockout mice, both epidermal and corneal wound healing is delayed, suggesting a common mechanism of action, which is possibly related to the lack of phosphatidylglycerol production in the AQP3-deficient epithelia. Because phosphatidylglycerol also accelerates corneal wound healing in vitro, it can be a safe and effective treatment for corneal wounds to hasten healing following trauma, infection or ophthalmic surgery.

Epidermal keratinocytes express the PLD isoform, PLD2, and this isoform contributes a large proportion of the measured basal PLD activity in these cells. In view of the (i) results indicating the ability of PLD to utilize glycerol to synthesize phosphatidylglycerol in vitro and in intact keratinocytes, (ii) data suggesting the colocalization of PLD2 and the glycerol channel, AQP3, in epidermal keratinocytes, (iii) data supporting the involvement of AQP3 in the PLD2-mediated generation of the novel signaling molecule phosphatidylglycerol, (iv) results consistent with a role for AQP3, glycerol and phosphatidylglycerol in mediating keratinocyte differentiation, the present invention discloses evidence supporting an ability of phosphatidylglycerol liposomes to promote epidermal wound healing and data indicating that wounding can inhibit the function of the PLD2/AQP3/PG signaling module to decrease phosphatidylglycerol synthesis.

To determine whether this module might operate in corneal epithelial cells, the ability of phosphatidylglycerol liposomes to alter corneal epithelial cell proliferation was examined. Thus, (egg) phosphatidylglycerol liposomes inhibit the proliferation of SV40-immortalized human corneal epithelial cells. The PLD2/AQP3/PG signaling module may regulate corneal epithelial cells, indicating that this novel signaling module is not limited to epidermal keratinocytes.

Treatment with Elevated $[Ca^{2+}]_e$ Increases PLD Activity and PG Production

The ability of PLD to utilize primary alcohols to catalyze the transphosphatidylation reaction instead of hydrolysis has provided a specific measure of PLD activity. Rather than ethanol or butanol, the more physiological primary alcohol, glycerol, might be the natural substrate for this reaction. Indeed, PLD utilizes glycerol as a primary alcohol for the transphosphatidylation reaction in intact cells and homogenates (63-65). This ability was demonstrated in vitro using PLD2-overexpressing Sf9 membranes (46). In intact keratinocytes treated for 24 hours with vehicle, 125 µM $Ca^{2+}$ or 250 nM 1,25-dihydroxyvitamin $D_3$, the addition of $[^3H]$ or $[^{14}C]$ glycerol resulted in the formation of radiolabeled phosphatidylglycerol, as well as to a lesser extent phosphatidic acid and phosphatidylcholine. Elevated $[Ca^{2+}]_e$ induced a significant increase, and 1,25-dihydroxyvitamin $D_3$ a decrease, in PG formation (46). The formation of radiolabeled phosphatidylglycerol in response to elevated $[Ca^{2+}]_e$ was also concentration dependent, with maximal production after a 24-hour exposure to approximately 125 µM $Ca^{2+}$ (46). This increase seemed to be mediated, at least in part, by PLD activation (46). Consistent with this interpretation, bacterial PLD could release a major portion of the radioactivity incorporated into the phosphatidylglycerol generated upon addition of $[^{14}C]$ glycerol, suggesting that this glycerol was indeed incorporated into the headgroup position. On the other hand, no increase in radiolabeled phosphatidylglycerol levels was observed when cells were stimulated acutely with TPA (46), although this treatment activates PLD as measured by radiolabeled phosphatidylethanol production (46, 66). Since (i) 1,25-dihydroxyvitamin $D_3$ and TPA decrease PG synthesis, (ii) PLD1, but not PLD2, expression and activity is increased by 1,25-dihydroxyvitamin $D_3$ (62) and (iii) TPA activates PLD1 to a greater extent than PLD2 (67), radiolabeled PG production upon exposure to glycerol may be a measure of PLD2 activation in keratinocytes. Thus, PLD2 and the glycerol uptake mechanism, AQP3, should be co-localized.

PLD2 Colocalizes with AQP3 in Caveolin-Rich Membrane Microdomains in Keratinocytes PLD2 and AQP3 might be colocalized to provide glycerol to PLD2 for the transphosphatidylation reaction to yield PG. Since PLD2 is known to be located in caveolin-rich membrane microdomains in the human keratinocyte HaCaT cell line (65), whether these two proteins were present in membrane microdomains in primary mouse keratinocytes was examined. Indeed, sucrose density ultracentrifugation with western blot analysis of each fraction demonstrated that both PLD2 and AQP3 are found in the light membrane fractions also enriched in caveolin-1 (34). Colocalization was further shown by co-immunoprecipitation studies of vesicle populations and by confocal immunocytochemistry. In addition, depletion of cholesterol from the microdomains with methyl-beta-cyclodextrin induces a similar movement of all three proteins to heavier membrane fractions (34). Finally, PLD2 and AQP3 were shown to co-immunoprecipitate from detergent-solubilized cell extracts (34), suggesting a protein-, rather than a lipid-, mediated interaction between these two proteins. Approximately equal amounts of AQP3 are immunoprecipitated by anti-AQP3 or anti-PLD2, whereas anti-PLD2 immunoprecipitates much greater quantities of PLD2 than does anti-AQP3. This result suggests that the majority of AQP3 associates with PLD2 but only a portion of cellular PLD2 interacts with AQP3. This interpretation is also supported by the distributions of these two proteins as visualized by confocal immunocytochemistry (34). This idea was confirmed by the finding that co-expression of PLD2 and AQP3 in Sf9 insect cells allowed co-immunoprecipitation of PLD2 by AQP3, and vice versa, but expression of both proteins was required for this co-immunoprecipitation (FIG. 9).

Inhibition of AQP3 Activity Decreases PG Synthesis in Keratinocytes

The aquaporins are a family of water and water/glycerol channels (37, 38). AQP3 is an aquaglyceroporin that transports glycerol efficiently but only weakly transports water (39) and is expressed in the basal layer (40), as well as suprabasal cells (41), of the epidermis. An AQP3 null mutant mouse has an abnormal epidermal phenotype, with dry skin, a reduced hydration capacity (43), delayed barrier recovery and wound healing and decreased elasticity, as well as a reduced epidermal glycerol content (44). These abnormalities were corrected by topical or oral application of glycerol but not related analogs (45). In lung epithelia AQP3-mediated glycerol uptake is inhibited by low pH (4-6.5) (68); this regulation by hydrogen ion concentration is potentially very important in skin, as the epidermis is known to exhibit regions of low pH in a developmentally regulated manner (69). Indeed, low pH inhibits both radiolabeled glycerol uptake and phosphatidylglycerol synthesis in keratinocytes (35). Therefore, PLD2 and AQP3 comprise a functional unit in that the aquaglyceroporin provides glycerol for use by PLD2 to produce phosphatidylglycerol.

Overexpression of AQP3 Increases Promoter Activity of Keratinocyte Differentiation Markers and Decreases Basal Cell Marker Promoter Activity To circumvent the difficulty of a relatively low transfection efficiency of primary cells, co-transfection of primary keratinocytes with both a plasmid encoding AQP3 (or the empty vector) and constructs in which the promoter for a marker of keratinocyte proliferation or differentiation controls the expression of a reporter gene was used. As cells generally take up both constructs, reporter gene expression should only be measured in those cells that also overexpress AQP3. Thus, primary mouse keratinocytes were co-transfected with the empty vector (pcDNA3) or a plasmid encoding AQP3 and a second plasmid bearing the reporter gene luciferase under the control of the keratin 5 or 10 promoter (provided by Dr. Bogi Andersen) or the involucrin promoter (provided by Dr. Daniel Bikle), as well as a third plasmid bearing Renilla luciferase for normalization purposes. After 48 hours, luciferase activities were determined, and normalized activities calculated. Overexpression of AQP3 decreased the promoter activity of the proliferative marker keratin 5 and increased the promoter activity of keratin 10, an early keratinocyte differentiation marker (35), while enhancing the stimulatory effect of elevated [Ca2+]e on involucrin promoter activity (35). These results suggest that AQP3 is involved in early keratinocyte differentiation, an interpretation consistent with the finding that PG production is greatest after stimulation with an intermediate Ca2+ concentration (46), known to induce maximal expression of the early differentiation markers keratin 1 and 10 (4).

Glycerol, but not Xylitol or Sorbitol, and PG Liposomes Inhibit Keratinocyte DNA Synthesis AQP3 and PLD2 may colocalize to provide glycerol for use by PLD2 in the transphosphatidylation reaction to generate phosphatidylglycerol, which then acts to promote early keratinocyte differentiation. This idea would predict that increasing the delivery of glycerol through the AQP3 channel or direct provision of phosphatidylglycerol itself should also trigger early differentiation. Since one of the first hallmarks of early differentiation is growth arrest and a reduction in DNA synthesis, the effect of exogenous glycerol (to enhance flux through the channel) on [3H]thymidine incorporation into DNA, a measure of DNA synthesis, was examined. Because osmotic stress is known to regulate keratinocyte function (70), to control for any osmotic effects of glycerol we also used equivalent concentrations of two other osmolytes, xylitol and sorbitol, as controls. Glycerol at concentrations from 0.1 to 1% inhibited DNA synthesis and enhanced the inhibitory effect of elevated $[Ca^{2+}]_e$, but similar concentrations of xylitol or sorbitol had little or no effect (35).

PG Liposomes Increase Proliferation in Slowly Growing Keratinocytes and Decrease Proliferation in Rapidly Growing Cells The effect of providing phosphatidylglycerol directly to keratinocytes in the form of liposomes was examined, since direct provision of phosphatidylglycerol itself should also trigger early differentiation. In highly proliferative cells, phosphatidylglycerol liposomes inhibit DNA synthesis. Moreover, this effect is not likely to represent toxicity since morphologic changes characteristic of cell death were not observed. To test the possibility that phosphatidylglycerol liposomes inhibit DNA synthesis non-specifically, keratinocytes were treated with liposomes formed from dioleoyl-phosphatidylpropranol (PP) and [3H]thymidine incorporation into DNA measured. Whereas PG liposomes inhibit DNA synthesis, phosphatidylpropanol liposomes have no effect on this parameter. The egg phosphatidylglycerol used in these experiments is composed primarily of the dioleoyl and dipalmitoyl species; therefore, that there is no effect of dipalmitoyl-PP on DNA synthesis was also determined. On the other hand, if phosphatidylglycerol liposomes are applied to keratinocytes with decreased proliferative capacity, presumably as the result of contact inhibition (and as indicated by reduced [3H]thymidine incorporation into DNA under control conditions), DNA synthesis is stimulated in a dose-dependent manner, with a half-maximal effect at a concentration of approximately 35_g/mL and a maximal stimulation at 100 μg/mL. These data provide additional evidence for a lack of toxicity of the phosphatidylglycerol liposomes on keratinocytes. Furthermore, this result suggests that phosphatidylglycerol has the capacity to normalize keratinocyte proliferation, inhibiting the proliferation of rapidly dividing cells and increasing proliferation in a setting of reduced growth.

PG and Glycerol Promoted Epidermal Wound Healing In Vivo

Verkman and colleagues observed that AQP3 knockout mice exhibit delayed wound healing (44). The present invention discloses that a mechanism underlying the slower wound healing in this mouse model is the lack of generation of the PG lipid signal. Thus, increasing the levels of PG might accelerate wound healing in normal epidermis. To test this idea, two full-thickness skin punch biopsies on either flank of two groups of mice were made. For one group the wounds were not treated or were treated with 2 M glycerol (in water as a positive control); for the other group the wounds were treated with either phosphate-buffered saline lacking divalent cations (PBS) or 100_g/mL phosphatidylglycerol liposomes in PBS. Wound healing was followed over four days using digital photography and computer image analysis.

FIGS. 2A-2B show a representative mouse from each group and FIG. 3 represents the cumulative results from eight mice per group, expressed as the percent of wound healing at day 4 relative to day 1 (to control for possible slight differences in the size of the initial wounds). PG liposomes significantly increased the rate of wound healing.

Cell Wounding Activated PLD but Inhibited PG Synthesis

Scraping or lifting cells from tissue culture dishes with a rubber policeman induces plasma membrane disruptions and cell wounding (72). In epidermal keratinocytes, the effect of such cell wounding on PLD activity was determined, as monitored by changes in radiolabeled phosphatidylethanol levels in [3H]oleate-prelabeled cells scraped or lifted from the dish in the presence of 0.5% ethanol. Controls included cells exposed to ethanol without scraping or lifting as well as cells released from the dish by trypsinization.

As shown in FIG. 4, cell wounding by scraping or lifting, but not trypsinization, activated PLD. In contrast and despite the increase in PLD activity, cell wounding inhibited the synthesis of radiolabeled phosphatidylglycerol (FIG. 4), suggesting a possible disruption of the interaction between AQP3 and PLD2. This result implies that direct provision of phosphatidylglycerol might be more effective and/or potent in terms of stimulating wound healing than providing glycerol, since the ability of AQP3 to "feed" the glycerol to PLD2 for phosphatidylglycerol synthesis would seem to be impaired. (Indeed, the concentration of 100 μg/mL phosphatidylglycerol used in the wound healing experiments is roughly equivalent to a concentration of 100 μM, which is approximately 10,000-fold less than the 2 M glycerol concentration that yielded an essentially equal acceleration of wound healing in skin in vivo.)

PG Liposomes and Glycerol Inhibit Corneal Epithelial Cell Proliferation

In an SV-40 immortalized human corneal epithelial cell line (73) (provided by Dr. Fu-Shin Yu, Wayne State University, Detroit, Mich.), the response to PG liposomes was examined. In proliferating corneal epithelial cells, liposomes composed of egg phosphatidylglycerol dose dependently inhibited DNA synthesis (as monitored by [3H]thymidine incorporation into DNA) with a half-maximal inhibitory concentration of approximately 30 μg/mL (FIG. 5). Glycerol and an elevated extracellular calcium concentration (1 mM versus a control calcium concentration of 90 μM) interacted to more efficiently inhibit DNA synthesis than either agent alone (FIG. 6). Finally, PLD2 and AQP3 localized to the same fractions upon sucrose density ultracentrifugation of SV40-immortalized human corneal epithelial cells suggesting that these two proteins may interact in corneal epithelial cells.

Thus, evidence suggests that the PLD2/AQP3/PG signaling module may be critically important in the early differentiative response of keratinocytes to elevated $[Ca^{2+}]_e$: (i) increased PLD activity is associated with induction of differentiation by other agents (66, 74); (ii) PLD2 is co-localized with AQP3 in lipid rafts (34), and these two proteins likely function in combination to increase phosphatidylglycerol formation (46), (ii) altering signal generation by the module by (a) overexpressing AQP3, (b) increasing glycerol influx or (c) providing phosphatidylglycerol directly alters early keratinocyte differentiation (35) and (iv) phosphatidylglycerol liposomes accelerate epidermal wound healing. The present invention discloses that this module and the resultant phosphatidylglycerol lipid signal are important in regulating corneal epithelial cell proliferation/differentiation as well. The ability of glycerol and PG liposomes to inhibit proliferation in a corneal epithelial cell model, as well as the report of Verkman's group that AQP3 knockout mice exhibit delayed corneal wound healing, indicates that this novel signaling module might be critically involved in other corneal epithelial cell responses, such as corneal wound healing.

PG Liposomes Enhance Corneal Wound Healing In Vitro

The present invention discloses that phosphatidylglycerol liposomes composed of some species (e.g., dioleoyl-phosphatidylglycerol) but not others (the mixture of phosphatidylglycerol species found in egg PG) can accelerate scratch wound healing of corneal epithelial cells in vitro. Transformed human corneal epithelial transformed human corneal epithelial cells were cultured in defined keratinocyte serum-free (dKSF) medium (Gibco). Sucrose gradient ultracentrifugation, immunoprecipitation and western blot analysis was used to detect the distribution and colocalization of PLD2 and AQP3 in the gradient fractions. DNA synthesis, measured as incorporation of [$^3$H]thymidine into DNA, was used as an index of cell proliferation. A wound closure assay was used to detect the effect of 0.1% or 0.5% glycerol, Ca plus 0.1% or 0.5% glycerol, egg phosphatidylglycerol, and DOPG on migration (and proliferation) of corneal epithelial cells. Confluent monolayers were scratched with a pipet tip and monitored over time for decreased width of the wound.

FIGS. 7A and 7B shows the effect of glycerol on wound closure in transformed human corneal epithelial cells. As shown in FIG. 7B, 0.05% glycerol and calcium significantly enhanced wound closure in transformed human corneal epithelial cells.

FIGS. 8A-8B show the effect of egg phosphatidylglycerol and dioleoylphosphatidylglycerol on wound closure in transformed human corneal epithelial cells. As is shown in FIG. 8B, 50 mg/ml of dioleoylphosphatidylglycerol significantly enhanced wound closure in transformed human corneal epithelial cells. In contrast, egg phosphatidylglycerol inhibited wound closure, clearly demonstrating the importance of the phosphatidylglycerol species in determining the effect on human corneal epithelial cell migration and wound healing.

The following references may have been cited herein:
1. Whitcher et al. 200. Bulletin of the WHO 79:214-221
2. Moshirfar et al. 2007. J Cataract Refract Surg 33:474-483
3. Bollag et al. 2004. Drug mNews Perspect 17:117-126
4. Yuspa et al. 1989 J Cell Biol 109:1207-1217
5. Bikle et al. 2001 Mol Cell Endocrinol 177:161-171
6. Menon G K, Elias P M 1991 Arch Dermatol 127:57-63
7. Menon et al. 1992 Cell Tissue Res 270:503-512
8. Menon et al. 1985 J Invest Dermatol 84:508-512
9. Menon et al. 1994 J Invest Dermatol 102:789-795
10. Oda et al. 2000 J Biol Chem 275:1183-1190
11. Oda et al. 1998 J Biol Chem 273:23344-23352
12. Komuves et al. 2002 J Cell Physiol 192:45-54
13. Harkin et al. 2004 Br J Ophthalmol 88:1154-1158
14. Tong et al. 2006 Invest Ophthalmol Vis Sci 47:1938-1946
15. Adhikary et al. 2004. Invest Ophthalmol Vis Sci 45:1080-1087
16. Umenishi et al. 1996. DNA Cell Biol 15:475-480
17. Hamann et al. 1998. Am J Physiol 274:C1332-C1345
18. Kawakita et al. 2004. Invest Ophthalmol Vis Sci 45:3507-3512
19. Lu et al. 2006. Eur J Cell Biol 85:803-811
20. Levin M H, Verkman A S 2006 Invest Ophthalmol Vis Sci 47:4365-4372
21. Exton J H 1994 Biochim Biophys Acta 1212:26-42
22. Nishizuka Y 1995 FASEB J 9:484-496
23. Brose N, Rosenmund C 2002 J Cell Sci 115:4399-4411
24. Yokozeki et al. 1998 J Neurochem 71:410-417
25. Rizzo 1999 J Biol Chem 274:1131-1139
26. Rizzo 2000 J Biol Chem 275:23911-23918
27. Kam Y, Exton J H 2001 Mol Cell Biol 21:4055-4066
28. Ha K S, Exton J H 1993 J Cell Biol 123:1789-1796
29. Sergeant et al. 2001 J Biol Chem 276:4737-4746
30. Fang et al. 2001 Science 294:1942-1945
31. McPhail et al. 1999 Biochim Biophys Acta 1439:277-290
32. Jones et al. 1999 Biochim Biophys Acta 1439:229-244
33. Liscovitch et al. 2000 Biochem J 345:401-415
34. Zheng X, Bollinger Bollag W 2003 J Invest Dermatol 121:1487-1495
35. Bollag 2007 J Invest Dermatol; Jun. 28, 2007
36. Bollag W B, Zheng X 2005 Phospholipase D and keratinocyte biology. In: Trends in Protein Research. New York: Nova Science Publishers, Inc.; pp 79-118
37. Verkman A S, Mitra A K 2000 Am J Physiol Renal Physiol 278:F13-F28
38. Borgnia et al. 1999 Annu Rev Biochem 68:425-458
39. Yang B, Verkman A S 1997 J Biol Chem 272:16140-16146
40. Matsuzaki et al. 1999 J Histochem Cytochem 47:1275-1286
41. Sougrat et al. 2002 J Invest Dermatol 118:678-685
42. Ma et al. 2000 Proc Natl Acad Sci USA m97:4386-4391
43. Ma et al. 2002 J Biol Chem 277:17147-17153
44. Hara M, Ma T, Verkman A S 2002 J Biol Chem 277:46616-46621
45. Hara M, Verkman A S 2003 Proc Natl Acad Sci USA 100:7360-7365
46. Zheng X, Ray S, Bollag W B 2003 Biochim Biophys Acta 1643:25-36
47. Murray N R, Fields A P 1998 J Biol Chem 273:11514-11520
48. Gökmen-Polar Y, Fields A P 1998 J Biol Chem 273:20261-20266
49. Pietromonaco et al. 1998 J Biol Chem 273:7594-7603
50. Klemm D J, Elias L 1988 Arch Biochem Biophys 265:506-513
51. Klemm D J, Elias L 1988 Exp Hematol 16:855-860
52. Klemm D J, Kazim A L, Elias L 1988 Arch Biochem Biophys 265:496-505
53. Bodin et al. 2001 Biochemistry 40:15290-15299
54. Sato et al. 2000 Proc Natl Acad Sci USA 97:10655-10660
55. Kruse et al. 2000 J Biol Chem 275:6509-6514
56. Piccotti et al. 2002 J Biol Chem 277:12075-12081
57. Lutter et al. 2000 Nature Cell Biol 2:754-756
58. Kuwana et al. 2002 Cell 111:331-342
59. Zhai et al. Eur J Biochem 268:48-55

60. Epand et al. 2002 J Biol Chem 277:32632-32639

Any patents or publications mentioned in this specification are indicative of the levels of those skilled in the art to which the invention pertains. These patents and publications are incorporated by reference herein to the same extent as if each individual publication was incorporated by reference specifically and individually. One skilled in the art will appreciate that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A method of treating a corneal disorder comprising administering to the eye of a patient in need thereof an ocular composition consisting of a pharmaceutically effective amount of dioleoylphosphatidylglycerol in the form of liposomes from about 10 μg/mL to about 1,000 μg/mL and a pharmaceutically acceptable carrier liquid, wherein the corneal disorder is selected from the group consisting of corneal ulcer, corneal erosion, and corneal abrasions.

2. The method of claim 1, wherein the composition is administered in an eye drop.

* * * * *